(12) United States Patent
Jesmonth

(10) Patent No.: US 7,506,547 B2
(45) Date of Patent: Mar. 24, 2009

(54) SYSTEM AND METHOD FOR GENERATING THREE-DIMENSIONAL DENSITY-BASED DEFECT MAP

(76) Inventor: Richard E. Jesmonth, 326 Deerpoint Dr., Gulf Breeze, FL (US) 32561

( * ) Notice: Subject to any disclaimer, the term of this patent is extended or adjusted under 35 U.S.C. 154(b) by 484 days.

(21) Appl. No.: 10/763,263

(22) Filed: Jan. 26, 2004

(65) Prior Publication Data

US 2005/0165576 A1 Jul. 28, 2005

(51) Int. Cl.
G01N 29/04 (2006.01)
A61B 5/05 (2006.01)
(52) U.S. Cl. .............................. 73/618; 73/625; 73/628; 600/426
(58) Field of Classification Search .................... 73/618, 73/625, 628; 600/424, 427, 429, 426; 606/130
See application file for complete search history.

(56) References Cited

U.S. PATENT DOCUMENTS

| | | | |
|---|---|---|---|
| 2,671,896 A | 3/1954 | de Rosa | |
| 3,587,107 A | 6/1971 | Ross | |
| 3,612,899 A | 10/1971 | Ross et al. | |
| 3,662,316 A | 5/1972 | Robbins | |
| 3,668,639 A | 6/1972 | Harmuth | |
| 3,678,204 A | 7/1972 | Harmuth | |
| 3,705,981 A | 12/1972 | Harmuth | |
| 3,728,632 A | 4/1973 | Ross | |
| 3,739,392 A | 6/1973 | Ross et al. | |
| 3,772,697 A | 11/1973 | Ross | |
| 3,806,795 A | 4/1974 | Morey | |
| 3,878,749 A | 4/1975 | Woron | |
| 3,934,252 A | 1/1976 | Ross et al. | |
| 3,995,212 A | 11/1976 | Ross | |
| 4,008,469 A | 2/1977 | Chapman | |
| 4,017,854 A | 4/1977 | Ross | |
| 4,072,942 A | 2/1978 | Alongi | |

(Continued)

FOREIGN PATENT DOCUMENTS

DE 4320039 12/1994

(Continued)

OTHER PUBLICATIONS

European Search Report for EP 05705755.6, dated Dec. 19, 2007.

(Continued)

*Primary Examiner*—Hezron E. Williams
*Assistant Examiner*—Jacques M. Saint-Surin
(74) *Attorney, Agent, or Firm*—Michele Van Patten Frank; Patton Boggs LLP

(57) ABSTRACT

A system for mapping a condition of a structure that includes a plurality of support members covered by a wall is disclosed and includes a computer processor having a memory, a two-dimensional model of the structure stored in the memory and a three-dimensional model generator operatively associated with the computer. A density sensor that includes an ultrasonic transducer is operatively connected to the computer processor and provided with an ultra wideband transmitter. A position locating system is provided for determining the position of the ultra wideband transmitter, and hence the density sensor, in a frame of reference and communicating the position to the computer processor which displays indications of density on a three-dimensional model of the structure. A method for mapping a condition of a structure is also disclosed.

21 Claims, 4 Drawing Sheets

U.S. PATENT DOCUMENTS

| | | |
|---|---|---|
| 4,099,118 A | 7/1978 | Franklin et al. |
| 4,152,701 A | 5/1979 | Mara et al. |
| 4,254,418 A | 3/1981 | Cronson et al. |
| 4,344,705 A | 8/1982 | Kompa et al. |
| 4,506,267 A | 3/1985 | Harmuth |
| 4,641,317 A | 2/1987 | Fullerton |
| 4,651,152 A | 3/1987 | Harmuth |
| 4,688,041 A | 8/1987 | Cronson |
| 4,695,752 A | 9/1987 | Ross et al. |
| 4,698,633 A | 10/1987 | Lamensdorf et al. |
| 4,743,906 A | 5/1988 | Fullerton |
| 4,751,515 A | 6/1988 | Corum |
| 4,809,554 A | 3/1989 | Shade et al. |
| 4,813,057 A | 3/1989 | Fullerton |
| 4,862,174 A | 8/1989 | Naito et al. |
| 4,895,025 A | 1/1990 | Betts |
| 4,907,001 A | 3/1990 | Harmuth |
| 4,941,356 A | 7/1990 | Pallaske |
| 4,979,186 A | 12/1990 | Fullerton |
| 5,005,416 A | 4/1991 | Vick et al. |
| 5,057,846 A | 10/1991 | Harmuth |
| 5,095,312 A | 3/1992 | Jehle et al. |
| 5,134,408 A | 7/1992 | Harmuth |
| 5,146,616 A | 9/1992 | Tang et al. |
| 5,148,174 A | 9/1992 | Harmuth |
| 5,148,175 A | 9/1992 | Woolfolk |
| 5,153,595 A | 10/1992 | Harmuth |
| 5,159,343 A | 10/1992 | Harmuth |
| 5,177,486 A | 1/1993 | Kim et al. |
| 5,216,429 A | 6/1993 | Nakagawa et al. |
| 5,216,695 A | 6/1993 | Ross et al. |
| 5,223,838 A | 6/1993 | Tang et al. |
| 5,227,621 A | 7/1993 | Kim et al. |
| 5,239,309 A | 8/1993 | Tang et al. |
| 5,248,975 A | 9/1993 | Schutz |
| 5,274,271 A | 12/1993 | McEwan |
| 5,285,668 A | 2/1994 | Tokai |
| 5,285,688 A | 2/1994 | Robbins et al. |
| 5,293,555 A | 3/1994 | Anthony |
| 5,307,079 A | 4/1994 | Ross et al. |
| 5,307,081 A | 4/1994 | Harmuth |
| 5,313,056 A | 5/1994 | Kim et al. |
| 5,319,218 A | 6/1994 | Kim et al. |
| 5,323,169 A | 6/1994 | Koslover |
| 5,332,938 A | 7/1994 | McEwan |
| 5,337,054 A | 8/1994 | Ross et al. |
| 5,345,471 A | 9/1994 | McEwan |
| 5,351,053 A | 9/1994 | Wicks et al. |
| 5,351,063 A | 9/1994 | Kim et al. |
| 5,361,070 A * | 11/1994 | McEwan ..................... 342/21 |
| 5,363,108 A | 11/1994 | Fullerton |
| 5,365,240 A | 11/1994 | Harmuth |
| 5,381,151 A | 1/1995 | Boles et al. |
| 5,389,939 A | 2/1995 | Tang et al. |
| 5,422,607 A | 6/1995 | McEwan |
| 5,455,593 A | 10/1995 | Ross |
| 5,457,394 A | 10/1995 | McEwan |
| 5,465,094 A | 11/1995 | McEwan |
| 5,471,162 A | 11/1995 | McEwan |
| 5,473,942 A | 12/1995 | Vick et al. |
| 5,479,120 A | 12/1995 | McEwan |
| 5,486,833 A | 1/1996 | Barrett |
| 5,493,691 A | 2/1996 | Barrett |
| 5,510,800 A | 4/1996 | McEwan |
| 5,512,834 A | 4/1996 | McEwan |
| 5,517,198 A | 5/1996 | McEwan |
| 5,519,342 A | 5/1996 | McEwan |
| 5,519,400 A | 5/1996 | McEwan |
| 5,521,600 A | 5/1996 | McEwan |
| 5,523,758 A | 6/1996 | Harmuth |
| 5,523,760 A | 6/1996 | McEwan |
| 5,526,694 A | 6/1996 | McEachern et al. |
| 5,543,799 A | 8/1996 | Heger |
| 5,563,605 A | 10/1996 | McEwan |
| 5,573,012 A | 11/1996 | McEwan |
| 5,576,627 A | 11/1996 | McEwan |
| 5,581,256 A | 12/1996 | McEwan |
| 5,586,145 A | 12/1996 | Morgan et al. |
| 5,589,838 A | 12/1996 | McEwan |
| 5,592,177 A | 1/1997 | Barrett |
| 5,592,774 A | 1/1997 | Galyon |
| 5,594,456 A | 1/1997 | Norris et al. |
| 5,602,964 A | 2/1997 | Barrett |
| 5,609,059 A | 3/1997 | McEwan |
| 5,610,611 A | 3/1997 | McEwan |
| 5,610,907 A | 3/1997 | Barrett |
| 5,630,216 A | 5/1997 | McEwan |
| 5,648,787 A | 7/1997 | Ogot et al. |
| 5,661,385 A | 8/1997 | McEwan |
| 5,661,490 A | 8/1997 | McEwan |
| 5,673,050 A | 9/1997 | Moussally et al. |
| 5,677,927 A | 10/1997 | Fullerton et al. |
| 5,682,164 A | 10/1997 | McEwan |
| 5,687,169 A | 11/1997 | Fullerton |
| 5,721,540 A * | 2/1998 | Ellis .......................... 340/988 |
| 5,748,891 A | 5/1998 | Fleming et al. |
| 5,760,308 A | 6/1998 | Beall et al. |
| 5,824,908 A | 10/1998 | Schindel et al. |
| 5,877,422 A | 3/1999 | Otomo |
| 5,899,018 A | 5/1999 | Gordon et al. |
| 5,901,516 A | 5/1999 | Watson |
| 5,950,356 A | 9/1999 | Nimocks |
| 6,001,383 A | 12/1999 | O'Brien et al. |
| 6,002,708 A | 12/1999 | Fleming et al. |
| 6,054,950 A | 4/2000 | Fontana |
| 6,158,272 A | 12/2000 | Berretta |
| 6,178,834 B1 | 1/2001 | Cates |
| 6,189,393 B1 | 2/2001 | Cates |
| 6,205,701 B1 | 3/2001 | Nimocks, III |
| 6,276,209 B1 | 8/2001 | Schafer et al. |
| 6,313,643 B1 | 11/2001 | Tirkel et al. |
| 6,352,703 B1 | 3/2002 | Henderson et al. |
| 6,367,330 B1 | 4/2002 | Schafer |
| 6,385,268 B1 | 5/2002 | Fleming et al. |
| 6,386,038 B1 | 5/2002 | Lewis, III et al. |
| 6,389,741 B2 | 5/2002 | Nimocks, III |
| 6,400,754 B2 | 6/2002 | Fleming et al. |
| 6,419,632 B1 | 7/2002 | Shiki et al. |
| 6,439,069 B1 | 8/2002 | Cates |
| 6,528,985 B1 | 3/2003 | Greuel et al. |
| 6,618,612 B1 * | 9/2003 | Acker et al. ................ 600/424 |
| 6,757,557 B1 * | 6/2004 | Bladen et al. ............... 600/424 |
| 6,883,375 B2 | 4/2005 | Dunegan |
| 6,977,504 B2 * | 12/2005 | Wright et al. ............... 324/326 |
| 7,085,400 B1 * | 8/2006 | Holsing et al. ............. 382/103 |
| 2001/0035050 A1 | 11/2001 | Kenney et al. |
| 2001/0047691 A1 | 12/2001 | Dzenis |
| 2002/0180607 A1 | 12/2002 | Donskoy et al. |
| 2003/0074953 A1 | 4/2003 | Glaser et al. |
| 2004/0125916 A1 * | 7/2004 | Herron et al. ................ 378/65 |
| 2004/0176931 A1 * | 9/2004 | Wright et al. ............... 702/189 |
| 2005/0077455 A1 * | 4/2005 | Townley-Smith et al. ................. 250/227.27 |
| 2005/0151649 A1 * | 7/2005 | Wright et al. ............ 340/572.2 |

OTHER PUBLICATIONS

Bucur, Voichita, Acoustics as a Tool for the Nondestructive Testing of Wood, NDT.net vol. 4 (11) Nov. 1999, 8 pages.

Development of AE Detector for Termite Attack http://h3news1.kais.kyoto-u.ac.jp/projects/bio/AE-detector2/e-index.html, 2 pages (1991).

Kabir et al., Time Domain Ultrasonic Signal Characterization for Defects in Thin Unsurfaced Hardwood Lumber, Wood and Fiber Science, vol. 34(1) Jan. 2002, pp. 165-182.

Kawamoto et al., Acoustic Emission And Acousto-Ultrasound Techniques For Wood And Wood-Based Composites-A Reveiw, US Department of Agriculture Forest Service, General Technical Report FPL-GTR-134 (Dec. 2002), 12 pages.

Pest Control Industry Representatives Address USDA Federal Research Conference http://www.lipca.com/pressrelease-3.php3, (2002), 2 pages.

Sandoz, J. L., Ultrasonic Solid Wood Evaluation in Industrial Applciations, NDTnet vol. 1 (12) Dec. 1996, 7 pages.

Sandoz et al., Standing Tree Quality Assessments Using Acousto-Ultrasonic, 9 pages.

Wormley, Sam, Ultrasonic Inspection of Wood, Dec. 14, 1995 nde.appliedphysics.swri.edu/pipermail/nde/1995-December/002025.html, 1 page.

International Search Report and Written Opinion for PCT/US05/01314, filed Feb. 21, 2007 (11 pages).

* cited by examiner

SYSTEM AND METHOD FOR GENERATING THREE-DIMENSIONAL DENSITY-BASED DEFECT MAP

BACKGROUND OF THE INVENTION

Field of the Invention

The present invention is directed to a method and system for inspecting structures for hidden defects and damage, and more particularly, to a method and system for displaying detected defects on a three-dimensional representation of a structure or a portion or element thereof.

The condition of structures such as single family homes, apartments, and commercial buildings is evaluated, or estimate when, for example, the building is sold, and/or used as collateral for a loan. The evaluation or estimation typically includes an inspection of the building. A major reason for the inspection, particularly for wood-framed homes and commercial buildings, is that the building may have been damaged by wood-eating insects, such as, for example, termites, or by wood damaging fungus, commonly called "wood rot." The damage is often hidden because wood frames are almost always concealed by, for example, drywall, paneling, clapboard, brick and other wall surface materials. Therefore, neither the existence of the damage, nor its extent, is generally visible without removing the covering material. In other words, an accurate determination of the existence of, and full extent of termite or wood rot damage to a typical wood-framed house or other wood-framed structure would require removing all of the wall covering, thereby rendering the entire frame visible. However it is generally not feasible, either practically or economically, to remove all the wall covering of a house or commercial building each and every time damage, such as termite or wood rot, requires assessment. This would essentially require destruction and rebuilding of a house each time its value needed accurate assessment.

Prior art methods exist for detecting damage caused by termite actively. One such method is acoustic emission detection, which senses the vibrations produced by termites when they break the cellulose and lignin fibers, i.e., eat the wood they are consuming, as described by, for example U.S. Pat. No. 4,895,025 issued Jun. 26, 1990. U.S. Pat. No.5,285,668 in the name of Robbins and Mueller describes another system for detecting wood-destroying insects by sensing acoustic emissions.

There are multiple shortcomings with the known acoustic emission methods. One is that acoustic emission techniques are prone to error due to ambient noise. Another is that termites are not always feeding. Still another is that termites may use extensive galleries to move between a feeding region and a nest, and acoustic emission methods may not detect termites within such galleries. A still further, and more significant shortcoming is that acoustic emission methods detect only the presence of feeding termites; they do not detect, much less give an accurate assessment of, the damage that the termites have caused in the past or damage produced by wood rot or resulting from other non-insect causes.

For the reasons above, building inspectors typically compromise by removing only a portion of the wall covering when performing an inspection or damage assessment. This practice of partial removal has two untoward effects. One is that even though the removal is limited there is still some damage to the building. A second, and perhaps more important negative effect is that significant damage may be overlooked. Therefore, the result of the partial removal is that either a buyer is faced with major repairs, or a lender is faced with a building having less collateral value than originally estimated.

Another shortcoming of existing methods is that the building inspector typically describes location and extent of the termite or wood rot damage verbally or using sketches. Rarely does an inspector have access to the complete architectural drawings of the house on which he could mark damaged areas to enable others to visualize the extent of the damage.

Still another shortcoming of existing inspection methods is that once a wood framed structure is completed it is virtually impossible to verify the integrity of the original construction methods through nondestructive means, e.g., it may be difficult or impossible to determine the fastener pattern used for securing the wall material to the underlying supports or studs and whether an adequate number of fasteners was used.

SUMMARY OF THE INVENTION

These problems and others are addressed by the present invention which, in a first aspect, comprises a method for detecting damage to a structure having a plurality of support members disposed between a first wall and a second wall. The method involves locating a first support member behind a wall and aligning a scanning device with the first support member. The scanning device includes an ultrasonic transducer and a detector for detecting ultrasonic energy. The scanning device is moved over the first wall while directing ultrasonic energy toward the first support member and detecting reflected ultrasonic energy. The reflected ultrasonic energy is analyzed to determine the relative density of the first support member in relation to a known density, and the position of the scanning device is recorded when the reflected ultrasonic energy indicates a density different from the known density.

Another aspect of the invention comprises a method for mapping a condition of a structure that includes a plurality of support members covered by at least one wall. A representation of the structure is stored in a computer, and support member density is measured at a plurality of sites on a plurality of support members. The location of each of the sites at which measured density varies from expected, normal density is identified, and these locations are mapped onto the representation of the structure to provide a visual indication of support member density at a number of locations.

In another aspect, the invention comprises a system for mapping a condition of a structure that includes a plurality of support members covered by a wall. The system includes a computer processor having a memory, a position locating system for determining the position of a marker in a frame of reference and communicating the position to the computer processor, a density sensor operatively connected to the computer processor, and a marker associated with the density sensor.

Another aspect of the invention is a system for mapping a condition of a structure that has a plurality of support members covered by a wall. The system includes a computer processor having a memory and a two-dimensional model of the structure stored in the memory. The computer is also provided with a three-dimensional model generator for generating a three-dimensional model of at least a portion of the structure from the two-dimensional model. The system further includes a density sensor and a position locating system for determining the position of the density sensor and communicating the position to the computer processor. The position location system comprises a plurality of ultra wideband receivers and an ultra wideband transmitter associated with the density sensor.

An additional aspect of the invention comprises a system for mapping a condition of a structure having a plurality of support members covered by a wall which uses a processing device, a position locating system for determining the position of a marker in a frame of reference and communicating the position to the processor device, a density sensing device operatively connected to the processor device, and a marker associated with the density sensing device.

BRIEF DESCRIPTION OF THE DRAWINGS

The present invention will be better understood after a reading and understanding of the following detailed description of the invention in connection with the below drawings wherein.

DETAILED DESCRIPTION OF THE INVENTION

Overview

Figure 1:
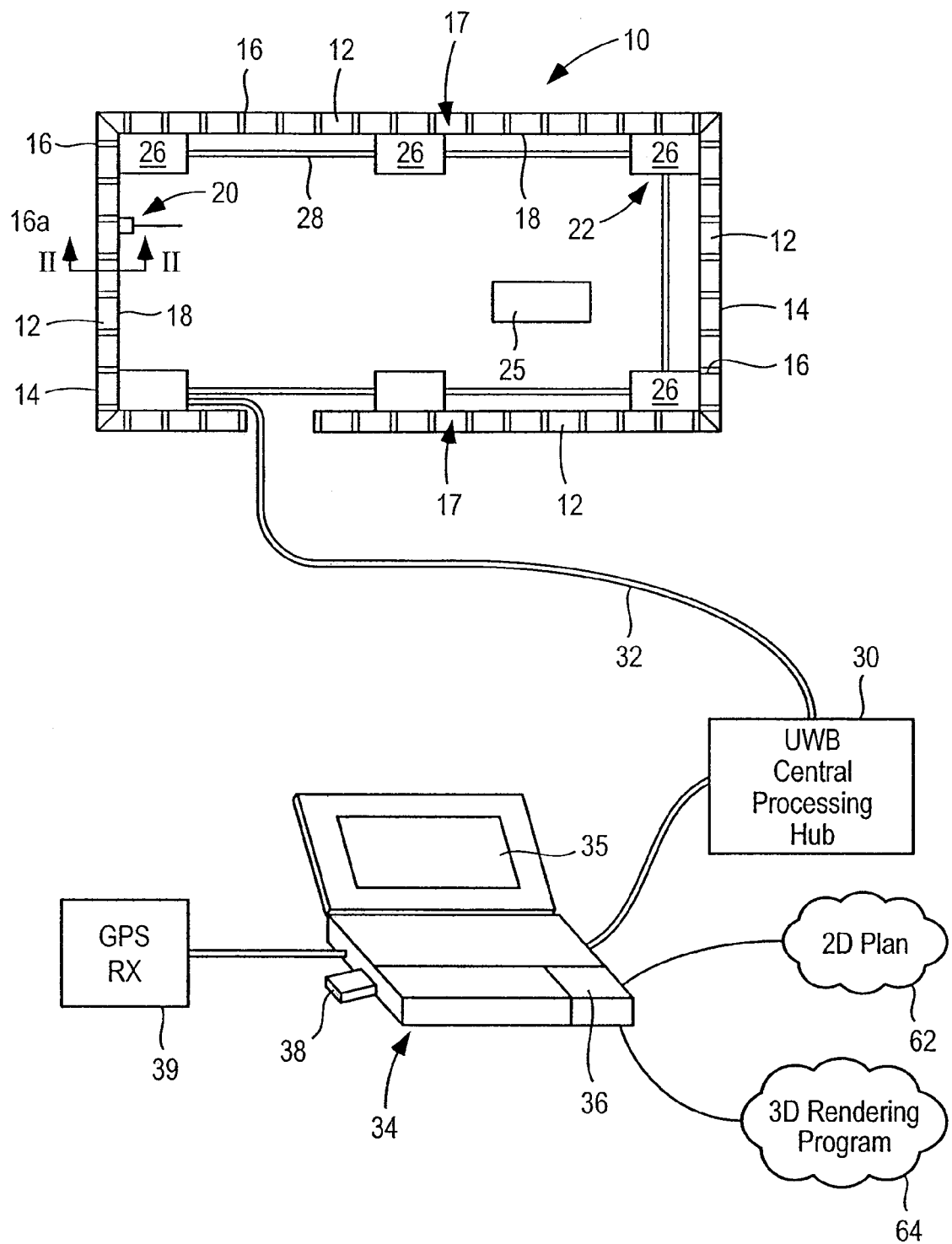
FIG. 1 is a schematic representation of a defect detecting system according to the present invention including a scanning device having a holder and showing a sectional plan view of a structure to be scanned.

A general example of the subject system includes a scanning device comprising a transmitter, including, for example an ultrasonic transducer, for transmitting acoustic signals into a portion of a structure and a receiver for receiving reflections of the acoustic signal, circuitry for comparing the reflected acoustic signals to reference signals produced by undamaged structural elements, and a wireless transmitter for sending time and relative density information to a central processing device such as a laptop computer. The system also includes a position detection system for detecting the position of the transmitter as it is moved throughout a structure and transmitting information concerning the position of the transmitter to the laptop computer. The computer includes instructions for associating the time and density information with the positional information and using this information to generate a density profile for a region from which the energy was reflected. The density profile may be superimposed over a three-dimensional representation of the structure being scanned to allow ready visualization of the portions of the structure where density varies from normal. The example apparatus may also include a display proximal to, or in the vicinity of, the acoustic transducer for displaying the density map to the user at the site of the inspection.

A general example of the described method includes moving the scanning device over a structure, such as a wall of a house, to obtain a density profile for desired portions of the structure and its internal framework. For example, an operator may place the scanning device into contact with one or more walls or the ceilings or floors of a house, or other structure, and move the sensor along the surface of such walls, ceilings or floors. Concurrent with the movement, an acoustic density sensor generates density data indicating the actual or relative density of material within a predetermined depth or distance into the structure. The density data is either stored in a storage unit within the acoustic density sensor for subsequent transfer to a computational unit, or transmitted to a remote storage unit or to the computational unit during the scanning. During the scanning operation, the density sensor position detector detects and records sensor position data indicating the location of the density sensor. The sensor position data and the density data are linked or otherwise associated with one another. The scanning is continued until the density profile for all, or for a desired portion of, the structure is obtained. A density map is generated, reflecting the density profile corresponding to each position, or region, over which the transducer was moved, the generation being based on the density data and the sensor position data. This density map may be superimposed over a three-dimensional computer model of the structure being scanned to allow a viewer to quickly locate portions of the structure where density deviates from normal.

DETAILED DESCRIPTION

Referring now to the drawings, wherein the showings are for the purpose of illustrating preferred embodiments only, and not for the purpose of limiting same, FIG. 1 shows a structure 10 to be scanned for damage. In this example, the structure is a rectangular wood frame house having four sides 12 each of which includes outer cladding 14, such as, for example, wood, vinyl, aluminum, or brick, studs 16, which may be two by fours separated by a known distance (16 inches on center, for example) and an inner wall 18 which may be formed from plaster, plasterboard or other materials appropriate for forming the inner wall of a building and secured to studs 16 using fasteners 19, shown in FIG. 2. The space between each pair of adjacent studs 16 is the wall interior volume 17, which may be filled with, for example, fiberglass insulation.

While example operations of the system and method described herein are in connection with the inspection of wall studs 16, the system and method could also be used to inspect floor or ceiling joists or other structural elements whether hidden behind an inner wall or not. Moreover, while the scanned elements may be referred to herein as "structural" or "support" elements, it is not necessary that the elements actually perform these roles; for example, the system could also be used to determine the condition of decorative elements of a building.

The invention comprises a system and method for detecting defects in a structure, an example being defects in studs 16 caused by, for example, termites, other insects or rot. This damage weakens the studs 16 and reduces the strength and value of structure 10. The system comprises a scanning device 20 and a scanning device preprocessor 21, best shown in FIGS. 3 and 2, respectively, and a position location system shown in FIG. 1 and designated generally by the numeral 22 for determining the real-time location of scanning device 20. Position location system 22 comprises a transmitter 24, preferably an ultra wideband transmitter appropriate for sending signals up to 70 or 80 feet, associated with scanning device 20, a reference marker 25 comprising an ultra wideband transmitter, a plurality of receivers 26 disposed in or near structure 10 and connected by, for example, a daisy chain Ethernet 28, and a central processing hub 30 also connected to one of the plurality of receivers, for example, by an Ethernet connection 32. Central processing hub 30 is serially connected to a computer device 34 such as, for example, a general-purpose commercially available laptop computer having a memory 36 and a wireless receiver 38, and running under a commercially available operating system.

With continuing reference to FIG. 1, a global positioning system (GPS) receiver 39 is connected to the laptop 34. The GPS 39 is contemplated as a preferred means to reference the position the reference marker 25, but alternate referencing schemes may be substituted. An example wireless receiver 38 uses an IEEE 802.11 wireless standard such as WiFi; however any system for sending and receiving wireless data that is appropriate for use over the distances discussed herein and that operates through building walls could alternately be used.

Figure 2:
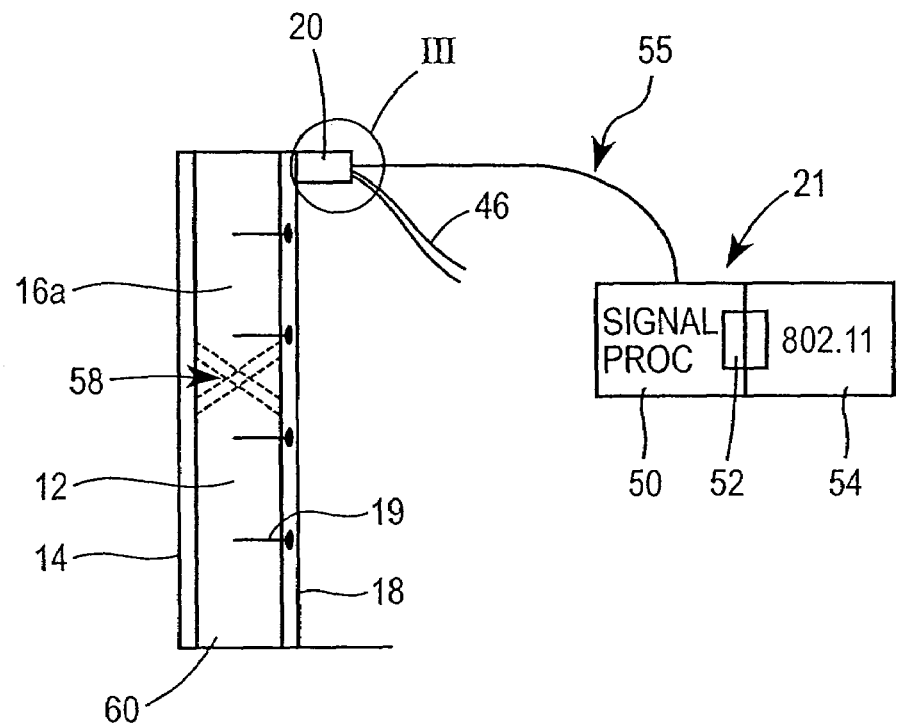
FIG. 2 is a sectional elevation view taken through line II-II in FIG. 1.
Figure 3:
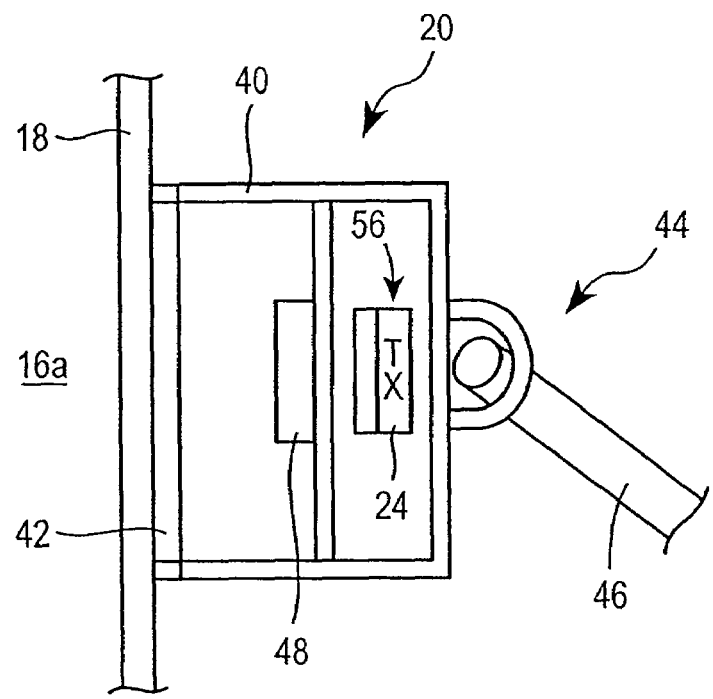
FIG. 3 is a detail view of circle III in FIG. 2.

Referring now to FIG. 3, an example scanning device 20 comprises a housing 40 including a wear plate 42 on a first side thereof, and a pivotable connector 44 on the opposite side that is connected to a handle 46. This arrangement allows housing 40 to be moved over the surface of a wall, such as inner wall 18, in carrying out the method of the present invention. Scanning device 20 includes an ultrasonic transducer 48 for sending and receiving ultrasonic signals. Referring to FIG. 2, the scanning device processor 21, which is shown separate from the scanning device 20, includes a signal processor 50 for processing the received signals and determining the density of the material that the signal has traversed relative to a known reference density. A signal cable 55 connects ultrasonic transducer 48 within the scanning device 20 to the scanning device processor 21. Devices for determining the actual density of the underlying material could be used as well, and as used herein, the phrase "density sensor" is intended to cover devices that measure either actual or relative density.

Commercially available ultrasonic sensors that implement both the scanning device 20 and the scanning device processor 21 and that can be used to measure density in this manner are known, and a suitable device is available from NDT James Instruments, Inc. of Chicago, Ill. under the trade name "James V-Mark II" with VC-4898 transducers. Examples of commercially available ultrasonic sensors, such as the James V-Mark II, currently implement the scanning device 20 and the scanning device processor 21 as separate physical units because, with current commercial technology, the combination being in a common housing may be overly massive for prolonged manual scanning operation. In the James V-Mark II and equivalent commercial units, the scanning device processor 21 is configured for hanging from the user's belt, or from the user's shoulder or neck using a strap. The cable 55 connection between the scanning device 20 and the scanning device processor 21 is implemented using a commercial electrical cable, either included with the commercial unit or readily selected by one of ordinary skill in the acoustic sensor arts.

When the material being scanned for density variations is wood, the transducer 48 is preferably operated in the pulse-echo mode using a carrier frequency of 54 KHz. This provides an acoustic emission that readily penetrates wood; the emission also has a wavelength of approximately three inches, which is large enough to penetrate anticipated size defects. Those skilled in the relevant arts will appreciate that changes in the carrier frequency might be needed when the material being sensed is a wood composite or other manufactured material. For ease of reference, all such materials will generally be referred to herein as "wood."

Referring to FIGS. 1 and 2, the signal processor 50 within the scanning device processor 21 is connected via an RS-232 serial interface 52 to a wireless transmitter 54 contained within the housing of the processor 21, which transmits information related to sensed density to wireless receiver 38 of laptop computer 34. One suitable method for transmitting such data is using ordered data pairs that comprise a time and a density measurement associated with that time. This information is stored in memory 36 of laptop 34 for further processing as will be described hereinafter. Alternately, information could be stored in scanning device 20 and later downloaded to computer 34 over a physical connection.

Referring to FIG. 1, position location systems such as system 22 are known, and a suitable system is available from Multispectral Solutions, Inc., of Germantown, Md. under the designation UWB Precision Asset Localization (PAL650). The operation and set-up of position locating systems 22 are known to persons skilled in the arts of position sensor location, and are described in the published literature. An example, identified for convenience, is a paper entitled "Commercialization of an Ultra Wideband Precision Asset Location System" by Robert J. Fontana, Edward Richley and JoAnn Barney presented at the 2003 IEEE Conference on Ultra Wideband Systems and Technologies in November 2003 in Reston, Va., which paper is hereby incorporated by reference.

The system of the present invention comprises a marker or tag 56 associated with scanning device 20 which tag comprises ultra wideband transmitter 24 operating, for example at 6 to 7 GHz. Ultra wideband receivers 26 are disposed in the vicinity of the structure being scanned. Six receivers 26 are shown in FIG. 1; however a different number and arrangement may be used for different building shapes and sizes. For example, it may be necessary to place additional receivers 26 in central locations, away from building walls, to ensure adequate coverage. These receivers may be disposed at different elevations to improve sensitivity to changes in the vertical position of tag 56, and generally should be spaced no more than about 75 feet apart. As described below, these receivers receive signals, comprising synchronization information, tag identification, and error correction information, from transmitter 24 and send information concerning time of signal receipt to processing hub 30. Processing hub 30 uses this time difference information to determine the position of the tag 56 in a frame of reference. The computer 34 uses the known location of reference marker 25 to relate this frame of reference to position of the system as determined by GPS receiver 39.

The operation of the present invention will be described below in connection with the scanning of a particular stud 16a shown in FIG. 2 which stud 16a is eight feet high and includes termite damage 58 in its midsection and rot damage 60 at its lower end.

Before the structure 10 can be scanned for hidden damage, the present system must be installed in or near structure 10 and calibrated. First, a plurality of ultra wideband receivers 26 are placed around the interior perimeter of the building being scanned, preferably inside the building at intervals no greater than about 75 feet. Additional receivers are placed throughout the building as needed to ensure that all parts of the building to be scanned are within about 75 feet of at least four receivers 26. This ensures that the signal transmitted by transmitter 24 is received by at least four receivers 26. The GPS receiver 39 is used to accurately determine the location of reference marker 25. Receivers 26 then measure the time at which a reference signal generated by reference marker 25 is received, and from this information, the position of each receiver 26 is determined with high accuracy.

Scanning device 20 is also calibrated by sensing the density of a reference material, which may be, for example, a stud 16 in one of the sides 12 of structure 10 that has been visually inspected and found to be undamaged. Alternately, density information for a variety of different materials may be stored in computer 34 and a reference density value can be selected from this stored data. Later sensing is not absolute; it is relative to this initially determined density. However, sensors that directly measure the absolute density of a material being scanned could be used without exceeding the scope of the present invention. Two-dimensional plans 62 of structure 10 are stored in memory 36 of laptop 34 along with a three-dimensional rendering program 64 that generates a three-dimensional representation of structure 10 or portions thereof from plans 62 or in any known manner.

After calibration, the position of stud 16a is determined in any well-known manner or by moving scanning device 20 normal to the direction of studs 16 until the density reading indicates that a stud 16, as opposed to a hollow space, has been detected. With scanning device 20 centered on stud 16a, scanning device 20 is placed at the top end of stud 16a, near the junction of inner wall 18 and a ceiling and is moved in a downwardly direction at a rate of, for example, approximately one half foot per second. Assuming a scan rate of approximately one half foot per second, an ultrasonic pulse repetition rate of about 10 Hz is used to ensure adequate density sampling as scanning device 20 moves along stud 16a at this rate. As scanning device 20 moves along stud 16a, it sends and receives pulses of ultrasonic energy that penetrate inner wall 18 and stud 16a; some of this energy is reflected by outer cladding 14 and by internal defects in stud 16 and returns to scanning device 20 where it is sensed.

Signal processor 50 within the scanning device processor 21 analyzes received signals and identifies signal variations indicative of a density that varies from the expected density determined during the calibration step. Signals that show the presence of a fastener 19, such as a nail or a screw, used to fasten wall 18 to stud 16a will also be received and can be used to plot the location of such fasteners 19 on a display. In this manner, the user can ensure that an adequate number of fasteners was used in securing inner wall 18 and that they were positioned correctly. Density information is then passed to wireless transmitter 54 via serial interface 52 and sent wirelessly to laptop computer 34, where time and density reading is stored as an ordered pair in memory 36. Alternately, a memory device (not shown) could be provided in the scanning device 20 for storing this information for later download to memory 36. Table 1 is populated with fictional data to illustrate how such received data might be interpreted.

TABLE 1

| Sensor Position | | | | Density | |
|---|---|---|---|---|---|
| t | x | y | z | t | d |
| 0 | 1 | 5 | 8 | 0 | 1.0 |
| 1 | 1 | 5 | 7.5 | 1 | 1.0 |
| 2 | 1 | 5 | 7.0 | 2 | 1.0 |
| 3 | 1 | 5 | 6.5 | 3 | 1.0 |
| 4 | 1 | 5 | 6.0 | 4 | 1.0 |
| 5 | 1 | 5 | 5.5 | 5 | 1.0 |
| 6 | 1 | 5 | 5.0 | 6 | 1.0 |
| 7 | 1 | 5 | 4.5 | 7 | 0.9 |
| 8 | 1 | 5 | 4.0 | 8 | .07 |
| 9 | 1 | 5 | 3.5 | 9 | .08 |
| 10 | 1 | 5 | 3.0 | 10 | 1.0 |
| 11 | 1 | 5 | 2.5 | 11 | 1.0 |
| 12 | 1 | 5 | 2.0 | 12 | 1.0 |
| 13 | 1 | 5 | 1.5 | 13 | 1.0 |
| 14 | 1 | 5 | 1.0 | 14 | 0.8 |
| 15 | 1 | 5 | 0.5 | 15 | 0.7 |
| 16 | 1 | 5 | 0.0 | 16 | 0.6 |

Referring now to FIG. 2 and Table 1, it can be seen that density measurements are taken at sixteen intervals as sensing device 20 moves from the top to the bottom of stud 16a. In the above table, "t" indicates a time measurement, "x," "y" and "z" are spatial coordinates of the scanning device 20 and "d" indicates a relative density measurement. Stud 16a is assumed to be eight feet long and is scanned in approximately 16 seconds; therefore, the measurements occur at roughly half-foot intervals. Again, the above data is for purposes of illustration only; actual data readings would occur approximately ten times per second and thus an anticipated scanning time of 16 seconds from floor to ceiling would generate about 160 data pairs. Moreover, some deviation in measurement is likely to occur due to lateral movement of scanner; therefore minor variations in density might be sensed even in an undamaged stud. Also, more frequent sampling would detect the presence of fasteners 19 in stud 16a. Representations 19' of fasteners 19 appear in FIG. 2, but are not apparent from the data in the above table.

As can be seen from the above data, the first six density readings, corresponding roughly to the upper three feet of stud 16, show that stud 16 is generally sound. In other words, the density of stud 16 does not deviate from the previously measured reference density. However, the next three readings, taken at times t=7, t=8 and t=9, show decreased density indicative of damage to stud 16a. This damage corresponds to termite damage 58 shown in FIG. 2. Density returns to normal at t=10 through t=13 and then decreases again at the last three readings, indicating further damage at the base of stud 16a. This damage corresponds to rot damage 60 at the base of stud 16a.

As the above density readings are being taken, the location of tag 56 is being tracked by position location system 22. Transmitter 24 in tag 56 sends periodic signals that are received by multiple receivers 26. The time that each signal from transmitter 24 arrives at each receiver 26 is accurately measured, and these times are transmitted over daisy chain Ethernet 28 to processing hub 30. Processing hub 30 uses these arrival times and the known location of each receiver 26 to calculate the position of tag 56. Accuracy to within about 2 cm is possible with current technology. The x, y and z coordinates of tag 56 at each measurement time are sent to laptop computer 34. Examples of such times and coordinates are also shown in Table 1; again, these data are for purposes of illustration only. Also, while the table suggests that the ultra wideband transmitter 24 and the wireless transmitter 54 are controlled by the same clock (which could be done with an appropriate system), in the preferred embodiment, real time positional information is received by laptop 34, and the actual position of tag 56 at the moment of each density measurement is extrapolated therefrom. This process is repeated for each stud 16 in structure 10.

Figure 4:
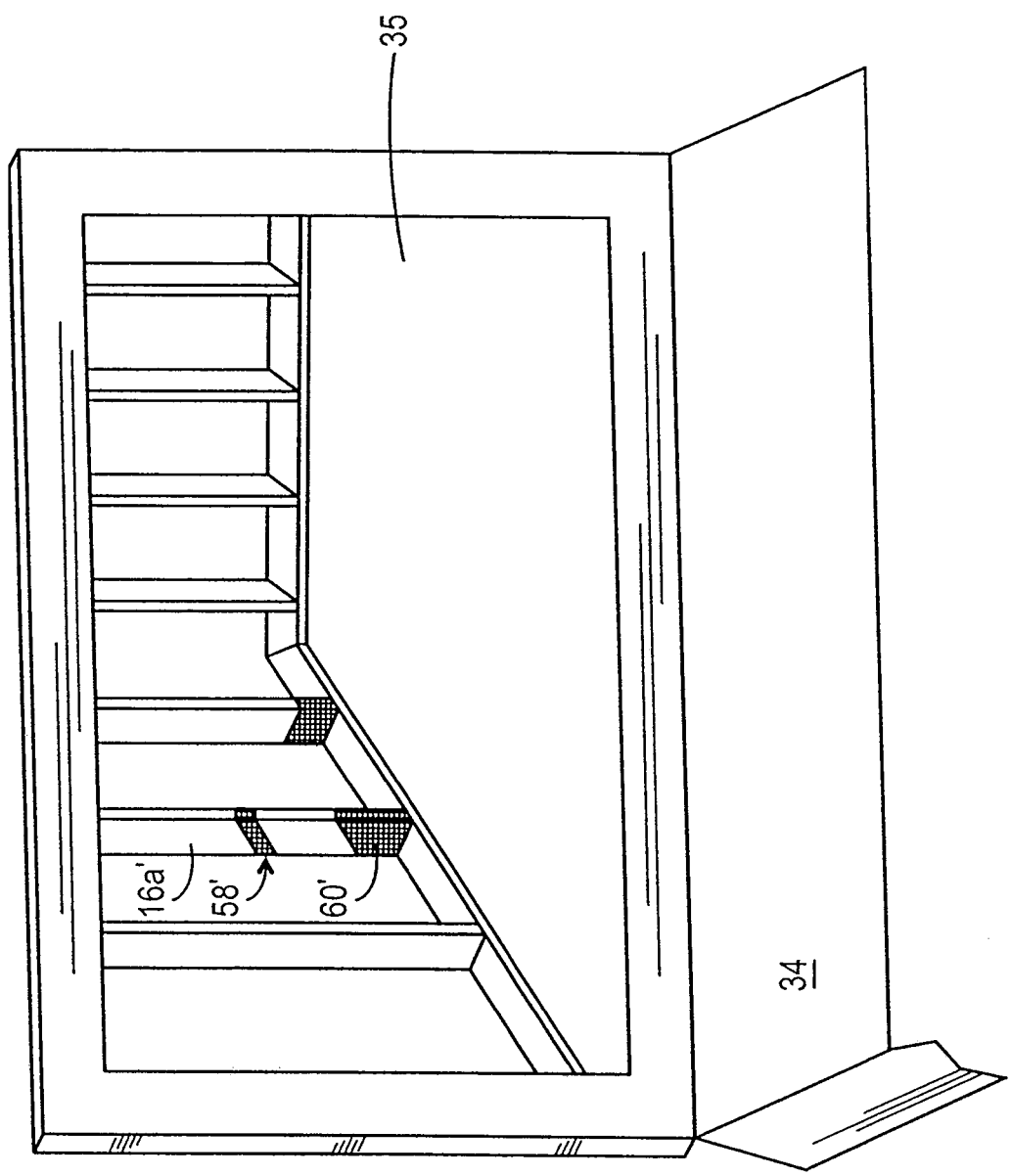
FIG. 4 shows an example of the type of display generated by the system of FIG. 1.

The data in Table 1 describes the density of elements in structure 10 at a large number of locations. These data are mapped onto a three-dimensional representation of structure 10 using three-dimensional rendering program 64 and displayed on laptop 34. An implementation of the rendering program is easily written by one of ordinary skill in the computer-aided design (CAD) arts. An example of such a display on the screen of laptop 34 is shown in FIG. 4 which includes an image 16a' of stud 16a showing a representation 58' of termite damage 58 and a representation 60' of rot damage 60. While cross-hatching is used in this figure, it is contemplated that different colors would be used to show different densities and density ranges and to indicate different degrees of damage. A viewer may use the three-dimensional rendering program to move through the virtual structure displayed on screen 35 and view the locations of damage. If desired, these areas may then be examined visually to further inspect the extent and nature of the damage detected. If no damage is found, however, one can be confident the structure is sound without causing any damage to the structure.

The above-described example scanning operation, as seen from the FIG. 4 depicted display, is in reference to the studs 16 shown in FIG. 1. The studs 16, however, are for purposes of example only. Referring to FIG. 1, the described method and system can also inspect, for example, the wall cladding 14. Such inspection may be particularly useful if the wall cladding 14 is plywood or oriented strand board (OSB), because termites may attack these materials prior to any detectable attack on the studs 16. A contemplated method for inspecting the cladding 14 is to position the scanning device 20 against an interior surface 18 of the outer wall, between studs 16, using the above-described calibration method. The scanning device 20 is then moved vertically near the junction of the floor (not numbered) to the ceiling (not numbered). As the scanning device 20 is moved, the ultrasound energy from the transmitter 24 passes through the drywall, through the air or fiberglass insulation between the studs, and strikes the cladding 14. As is known in the arts of acoustic density detection, at each interface between media, such as the interface between the inner wall 18 and the wall interior volume 17, and the interface between the interior volume 17 and the outer cladding 14, energy is reflected back to the acoustic receiver 56. The calibration is with respect to the significant reflection at the interface between the wall interior volume 17 and the outer cladding 14, due to the sharp discontinuity in density at the interface. Variations in the density of the cladding 14, though, such as caused by termite damage, will result in a corresponding change in the intensity of the reflected energy, which will manifest as shown in Table I above. Therefore, by vertically scanning the inner wall surface 18, at accessible locations that are between adjacent studs 16, a substantial percentage of the outer cladding 14 can be inspected for defects, without having to remove the aluminum siding, brick siding or other exterior materials.

Figure 5:
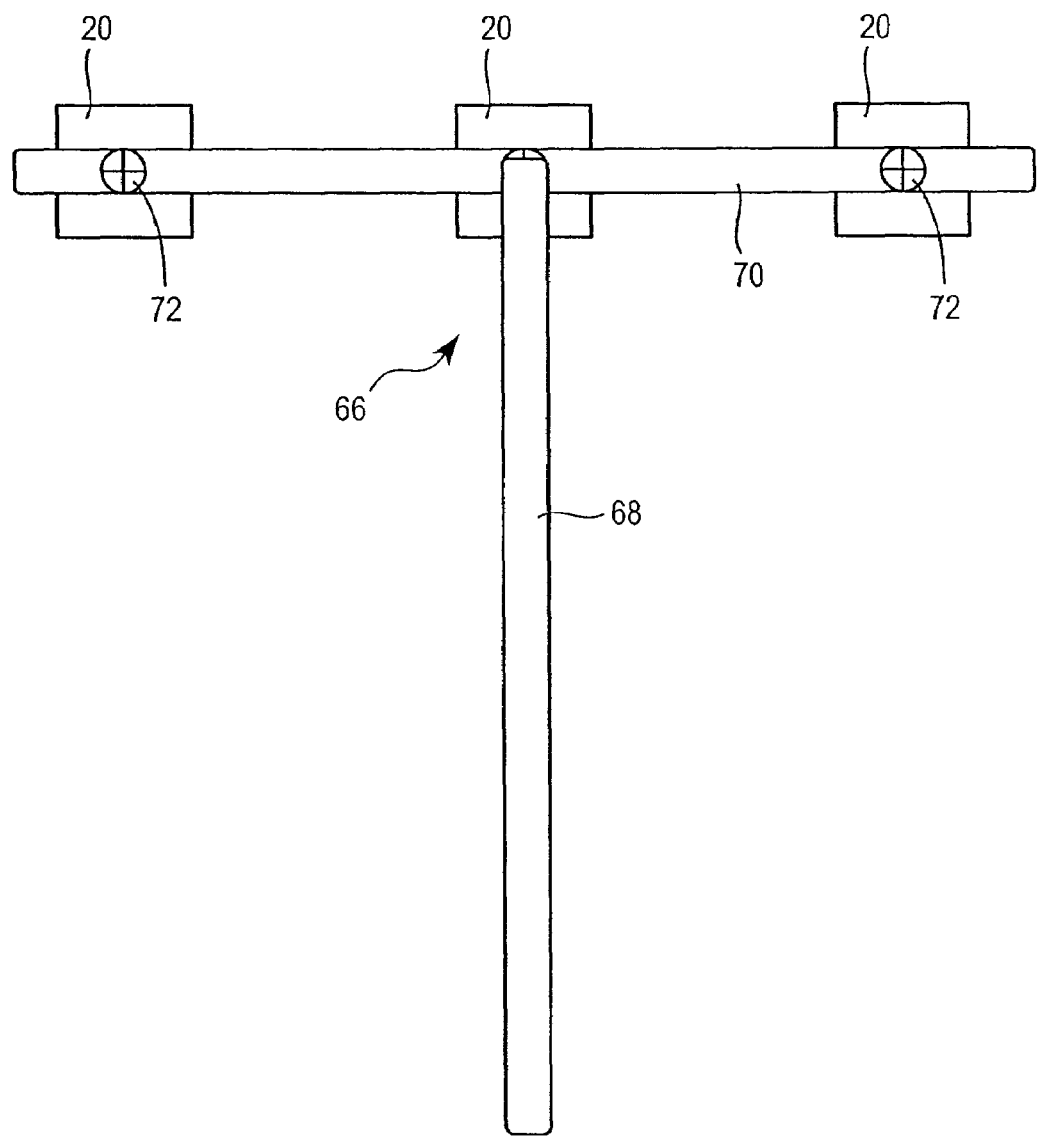
FIG. 5 is an elevational view of an alternative holder for holding several of the scanning devices shown in FIG. 1.

FIG. 5 shows a modified holder 66 for use with a system according to the present invention which comprises a handle 68 and a slide bar 70 mounted perpendicularly to handle 68 on which a plurality of scanning devices 20 can be mounted at various spacings, and secured thereto by a releasable fittings 72. For example, the device in FIG. 5 shows three scanning devices 20 attached to slide bar 70 at sixteen inch intervals, the on-center spacing between typical studs 16 in a structure. The spacing can be varied depending on the spacing of the elements being scanned, and additional scanning devices can be used if desired. As described above, each scanning device 20 includes a tag 56; in this example, each tag broadcasts a unique ID that is recognized by position locating system 20. The system of the present invention operates in the same manner as described above but at three times the speed because three studs 16 or other structural elements are scanned simultaneously using this system.

The present invention has been described herein in terms of a preferred embodiment. Modifications and additions to this embodiment will become apparent to those skilled in the relevant arts upon a reading and understanding of the foregoing description. For example, while the receivers 26 described above are connected by a daisy chain Ethernet, a hub and spoke or other arrangement could also be used. Moreover, various wireless transmission standards may be used for sending time and density information to laptop computer 34. And, while the present invention uses plans of the structure being measured to generate a three-dimensional representation of the structure, much information concerning the location of studs and the overall layout of the structure can be obtained directly from the positional measurements taken by the location system 22. It therefore may be possible to generate a three-dimensional representation of a structure directly from the measured position of scanning device 20 during the scanning process.

Further, the above-described examples employ a computer 34 such as a laptop, having the processing and display capability for receiving the data from the scanning device 20 and for generating a density table, mapping the data onto a three-dimensional structure 10, and displaying the results. A contemplated alternative is to substitute a data collection device for the laptop computer 34, and transfer the collected data to an off-site computer to generate the density table and to map the table onto a three-dimensional structure 10. The transfer may be in the form of a wired connection, removable media such as a zip drive, a line-of-sight wireless connection, or by satellite uplink. It is intended that all such obvious modifications and additions form a part of the present invention to the extent they come within the scope of the several claims appended hereto.

I claim:

1. A method for detecting damage to a structure comprising a plurality of support members disposed between a first wall and a second wall comprising:
   providing a scanning device comprising an ultrasonic transducer and a detector for detecting ultrasonic energy;
   locating a first support member behind the first wall;
   placing the scanning device adjacent the first wall in alignment with the first support;
   moving the scanning device over the first wall while directing ultrasonic energy toward the first support member and detecting reflected ultrasonic energy;
   analyzing the reflected ultrasonic energy to determine the relative density of the first support member in relation to a known density; and
   recording the position of the scanning device when the reflected ultrasonic energy indicates a density different from the known density.

2. The method of claim 1 further including calibrating the scanning device against a reference to determine the known density.

3. The method of claim 1 further including generating a representation of the first support member and an indication of the relative density of the first support member at each of a plurality of locations on the first support member.

4. The method of claim 3 further including detecting the presence of fasteners in the first support member and generating a representation of the fasteners on the generated representation of the first support member.

5. The method of claim 1 wherein said recording the position of the scanning device comprises providing a position locating system for determining the position of a marker and associating a marker with the scanning device.

6. The method of claim 5 wherein said marker comprises an ultra wideband transmitter and wherein said providing a position locating system comprises providing a plurality of ultra wideband receivers, connecting the ultra wideband receivers to a processor and calculating the time of arrival of a signal from said ultra wideband transmitter at a subset of said plurality of ultra wideband receivers.

7. The method of claim 1 further including detecting the presence of fasteners in the first support member.

8. The method of claim 1 wherein said generating a representation of the first support member comprises the steps of providing a two-dimensional representation of the structure and providing a program for generating a three-dimensional representation of the structure based on the two-dimensional representation of the structure.

9. The method of claim 1 further including wirelessly transmitting a signal indicative of the reflected ultrasonic energy to a computer having a processor.

10. A method for mapping a condition of a structure including a plurality of support members covered by at least one wall comprising:
- storing a representation of a structure in a computer;
- detecting support member density at a plurality of sites on a plurality of support members;
- identifying the location of each of the plurality of sites;
- mapping the plurality of sites onto the representation of the structure; and
- indicating on the representation of the structure the support member density at each of the sites.

11. The method of claim 10 wherein said measuring support member density at a plurality of sites on a plurality of support members comprises providing an ultrasonic transducer and transmitting an ultrasonic pulse through the at least one wall and each of the plurality of sites on each of the plurality of members and detecting reflection of the ultrasonic pulse.

12. The method of claim 11 wherein said identifying the location of each of the sites comprises providing a position locating system for determining the position of a marker in a frame of reference, associating a marker with the ultrasonic transducer, and recording the position of the marker in the frame of reference when the ultrasonic transducer is located at each of the plurality of sites.

13. The method of claim 12 wherein said indicating on the representation of the structure the support member density at each of the sites comprises displaying one of a plurality of colors associated with a plurality of predetermined density ranges at a location on the representation corresponding to one of the plurality of sites.

14. A system for mapping a condition of a structure comprising a plurality of support members comprising:
- a computer processor;
- a two-dimensional model of the structure operatively associated with said computer processor;
- a three-dimensional model generator operatively associated with said computer processor;
- a position locating system for determining the position of a marker in a frame of reference and communicating said position to said computer processor, said position locating system comprising a plurality of ultra wideband receivers;
- a density sensor comprising an ultrasonic transducer in communication with said computer processor; and
- an ultra wideband transmitter associated with said density sensor.

15. The system of claim 14, wherein the position locating system is a global positioning system.

16. A method for detecting damage to one of a first wall and a second wall facing one another and enclosing a plurality of support members:
- providing a scanning device comprising an ultrasonic transducer and a detector for detecting ultrasonic energy;
- locating a first support member behind the first wall;
- placing the scanning device adjacent the first wall laterally displaced from the first support;
- moving the scanning device over the first wall while directing ultrasonic energy toward the second wall and detecting reflected ultrasonic energy;
- analyzing the reflected ultrasonic energy to determine the relative density of the second wall in relation to a known density; and
- recording the position of the scanning device when the reflected ultrasonic energy indicates a density different from the known density.

17. A method according to claim 16, further comprising locating a second support member behind the first wall, wherein the placing the scanning device adjacent the first wall laterally displaced from the first support places the scanning device at a position aligned between said first support member and said second support member.

18. The method of claim 16 wherein said recording the position of the scanning device comprises providing a position locating system for determining the position of a marker and associating a marker with the scanning device.

19. The method of claim 18 wherein said marker comprises an ultra wideband transmitter and wherein said providing a position locating system comprises providing a plurality of ultra wideband receivers, connecting the ultra wideband receivers to a processor and calculating the time of arrival of a signal from said ultra wideband transmitter at a subset of said plurality of ultra wideband receivers.

20. The method of claim 17 wherein said recording the position of the scanning device comprises providing a position locating system for determining the position of a marker and associating a marker with the scanning device.

21. The method of claim 20 wherein said marker comprises an ultra wideband transmitter and wherein said providing a position locating system comprises providing a plurality of ultra wideband receivers, connecting the ultra wideband receivers to a processor and calculating the time of arrival of a signal from said ultra wideband transmitter at a subset of said plurality of ultra wideband receivers.

* * * * *